(12) United States Patent
Stone et al.

(10) Patent No.: US 9,412,560 B2
(45) Date of Patent: Aug. 9, 2016

(54) BULK DEPOSITION FOR TILTED MILL PROTECTION

(71) Applicant: FEI Company, Hillsboro, OR (US)

(72) Inventors: Stacey Stone, Portland, OR (US); Sang Hoon Lee, Hillsboro, OR (US); Jeffrey Blackwood, Portland, OR (US); Michael Schmidt, Gresham, OR (US)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/432,730

(22) PCT Filed: Oct. 7, 2013

(86) PCT No.: PCT/US2013/063704
§ 371 (c)(1),
(2) Date: Mar. 31, 2015

(87) PCT Pub. No.: WO2014/055982
PCT Pub. Date: Apr. 10, 2014

(65) Prior Publication Data
US 2015/0243477 A1    Aug. 27, 2015

Related U.S. Application Data

(60) Provisional application No. 61/710,376, filed on Oct. 5, 2012.

(51) Int. Cl.
*H01J 37/31* (2006.01)
*G01N 1/32* (2006.01)
(Continued)

(52) U.S. Cl.
CPC .............. *H01J 37/3005* (2013.01); *G01N 1/32* (2013.01); *G01N 23/2255* (2013.01);
(Continued)

(58) Field of Classification Search
CPC ............. G01N 1/32; G01N 1/26; G01N 1/28; G01N 23/2255; H01J 37/3056; H01J 37/3053; H01J 37/3005; H01J 37/31; H01J 37/3178; H01L 21/02636
USPC ........... 250/307, 492.3, 310, 492.1, 311, 306, 250/396 R, 442.11; 204/192.34, 192.33, 204/298.32, 192.11, 192.3, 192.32, 192.35
See application file for complete search history.

(56) References Cited

U.S. PATENT DOCUMENTS 5,435,850 A   7/1995   Rasmussen
5,851,413 A   12/1998  Casella et al.
(Continued)

FOREIGN PATENT DOCUMENTS

WO   2014106200   7/2014
WO   2014106202   7/2014

OTHER PUBLICATIONS

Lorenz Lechner, et al., "Improved Focused Ion Beam Target Preparation of (S)TEM Specimen—A Method for Obtaining Ultrathin Lamellae," Microscopy and Microanalysis, Apr. 18, 2012, pp. 379-384, vol. 18, Issue 2, Center for Electron Microscopy, Materials Science Group, Ulm University, Ulm, Germany.

*Primary Examiner* — David A Vanore
(74) *Attorney, Agent, or Firm* — Scheinberg & Associates, PC; Michael O. Scheinberg; John E. Hillert

(57) ABSTRACT

To reduce artifacts in a surface exposed by a focused ion beam for viewing, a trench is milled next to the region of interest, and the trench is filled to create a bulkhead. The ion beam is directed through the bulkhead to expose a portion of the region of interest for viewing. The trench is filled, for example, by charged particle beam-induced deposition. The trench is typically milled and filled from the top down, and then the ion beam is angled with respect to the sample surface to expose the region of interest.

20 Claims, 15 Drawing Sheets

(51) Int. Cl.
  *H01J 37/30* (2006.01)
  *G01N 23/225* (2006.01)
  *H01J 37/305* (2006.01)

(52) U.S. Cl.
  CPC ........ *H01J 37/3007* (2013.01); *H01J 37/3053* (2013.01); *H01J 37/3056* (2013.01); *H01J 37/31* (2013.01); *G01N 2223/104* (2013.01); *G01N 2223/611* (2013.01); *H01J 2237/063* (2013.01); *H01J 2237/08* (2013.01); *H01J 2237/2813* (2013.01); *H01J 2237/31732* (2013.01); *H01J 2237/31745* (2013.01); *H01J 2237/31749* (2013.01)

(56) References Cited

U.S. PATENT DOCUMENTS

| | | | |
|---|---|---|---|
| 6,211,527 B1 | 4/2001 | Chandler | |
| 6,373,070 B1 | 4/2002 | Rasmussen | |
| 6,621,081 B2* | 9/2003 | Moran | G21K 5/02 250/307 |
| 7,611,610 B2* | 11/2009 | Nadeau | G11B 5/3163 204/192.3 |
| 8,163,145 B2* | 4/2012 | Nadeau | G11B 5/3163 204/192.34 |
| 8,822,921 B2* | 9/2014 | Schmidt | G01N 1/286 250/306 |
| 8,859,963 B2* | 10/2014 | Moriarty | G01N 1/286 250/307 |
| 8,859,998 B2* | 10/2014 | Blackwood | G01N 1/286 250/492.1 |
| 8,912,490 B2* | 12/2014 | Kelley | G01N 1/32 250/306 |
| 9,111,720 B2* | 8/2015 | Kelley | G01N 1/32 |
| 2005/0012512 A1 | 1/2005 | Kolachina et al. | |
| 2005/0103746 A1* | 5/2005 | Nadeau | G11B 5/3163 216/62 |
| 2005/0109956 A1 | 5/2005 | Lundquist et al. | |
| 2006/0186336 A1 | 8/2006 | Giannuzzi et al. | |
| 2006/0284115 A1 | 12/2006 | Kaneoka et al. | |
| 2009/0242759 A1 | 10/2009 | Bray et al. | |
| 2011/0240852 A1 | 10/2011 | Tanner | |
| 2012/0199923 A1 | 8/2012 | Nadeau et al. | |
| 2013/0143412 A1* | 6/2013 | Moriarty | G01N 1/286 438/759 |
| 2013/0186747 A1* | 7/2013 | Schmidt | G01N 1/286 204/192.33 |
| 2013/0214468 A1* | 8/2013 | Giannuzzi | H01J 37/20 269/287 |
| 2013/0248354 A1 | 9/2013 | Keady et al. | |
| 2013/0319849 A1* | 12/2013 | Fuller | H01J 37/3026 204/192.34 |
| 2013/0328246 A1 | 12/2013 | Wells et al. | |
| 2014/0138350 A1* | 5/2014 | Kelley | G01N 1/32 216/37 |
| 2014/0190934 A1* | 7/2014 | Schmidt | G01N 1/286 216/37 |
| 2015/0137003 A1* | 5/2015 | Liew | H01J 37/305 250/453.11 |
| 2015/0243477 A1* | 8/2015 | Stone | G01N 23/2255 250/310 |
| 2015/0243478 A1* | 8/2015 | Lee | H01J 37/3056 204/192.11 |
| 2015/0276567 A1* | 10/2015 | Schmidt | G01N 1/32 250/307 |
| 2015/0330877 A1* | 11/2015 | Schmidt | G01N 1/28 438/696 |
| 2015/0340235 A1* | 11/2015 | Lee | H01L 21/0262 438/758 |

\* cited by examiner

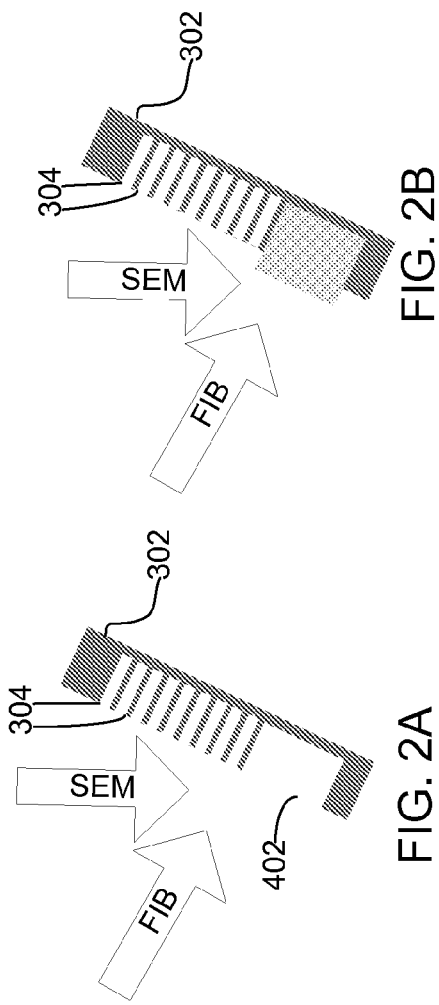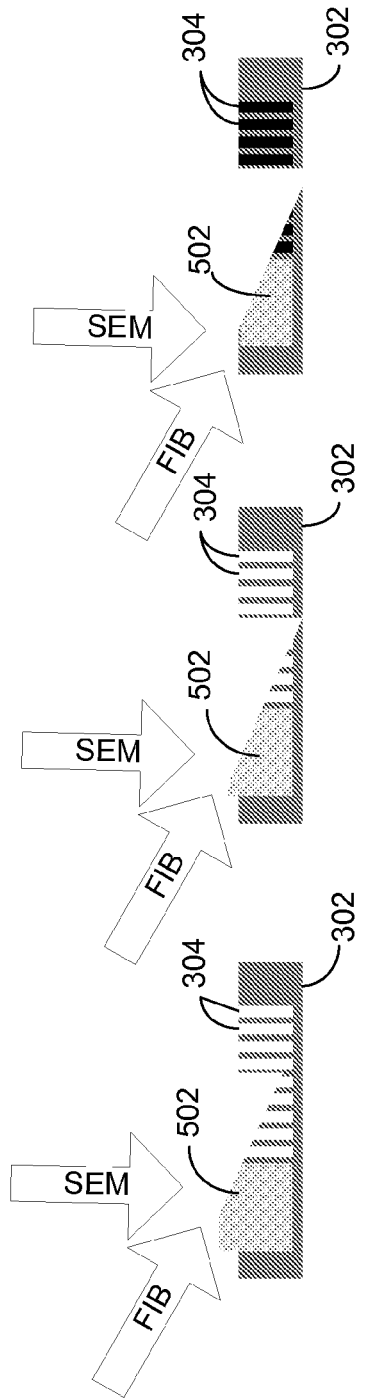

BULK DEPOSITION FOR TILTED MILL PROTECTION

TECHNICAL FIELD OF THE INVENTION

The present invention relates to charged particle beam processing of structures.

BACKGROUND OF THE INVENTION

A common method of examining microscopic (including nanometer scale) structures for process monitoring and failure analysis is to cut a trench in the structure with a focused ion beam (FIB) to expose a cross section orthogonal to the surface, and then view the cross section with a scanning electron microscope (SEM). Another technique is to extract a thin sample from the structure to view on a transmission electron microscope (TEM). Ion beam milling artifacts, however, can distort the exposed structure so that the electron beam image does not accurately represent the original structure.

One type of artifact is referred to as "curtaining," because it can look like a curtain. Curtaining occurs when different materials are removed at different rates, such as when the sample is composed of materials that are milled at different rates by the ion beam. Unfilled holes can cause curtaining, as can the milling by the "tails" of the Gaussian shaped ion beam. Curtaining can also occur when milling a surface that has an irregular shape. Sometimes a protective layer is deposited on top of the region of interest to reduce curtaining from the milling caused by the tail of the Gaussian-shaped beam as described, for example, in U.S. Pat. Pub. No. 20130143412 for "Methods for Preparing Thin Samples for Tem Imaging" and U.S. Pat. Pub. No. 20120199923 for "Method and Apparatus for Controlling Topographical Variation on a Milled Cross-Section of a Structure," both of which are assigned to the assignee of the present invention.

Severe artifacts can be created when exposing a feature having a height that is much greater than its width. Such a structure is referred to as a "high aspect ratio" feature. For example, a feature having a height four times greater than its width would be considered a high aspect ratio feature. Holes or contacts between layers in an integrated circuit are often high aspect ratio structures, having heights that are several times greater than their widths.

As semiconductor fabrication processes pack more circuitry into smaller packages, integrated circuit designs are becoming more three-dimensional (3D) and incorporate more high aspect ratio features. In analyzing high aspect ratio structures, especially unfilled contact holes, for the 3D integrated circuit (IC) structures such as 3D NAND circuits, conventional ion beam sample preparation causes unacceptable artifacts, such as distortion and curtaining.

When there are unfilled high aspect ratio holes on a sample, there are large differences in the milling rates between the solid regions and the regions adjacent to the unfilled hole. The large difference in milling rates results in curtaining or waterfall effects, another artifact that distorts the shape of the hole. Structure damage and artifacts from the ion beam milling process make it difficult to analyze high aspect ratio vertical structures.

One structural feature that process engineers need to observe is a through-silicon via (TSV). Cross-sectioning TSVs is a common practice in semiconductor labs to characterize voids and surface interfaces. Due to the depth of TSVs, typically 50-300 nm, milling a cross section of a TSV with an ion beam can result in substantial curtaining.

Because of the damage and artifacts caused by the use of ion beam milling to expose features, the images do not faithfully show the results of the fabrication process. The artifacts interfere with measurements and with an assessment of the fabrication process because the image and measurements show the effects of the sample preparation, as well as the result of the original fabrication process.

High aspect ratio holes or trenches with complex material stacks are also difficult to measure with other known methods, such as scatterometry and critical dimension scanning electron microscopy (CD-SEM).

What is needed is a way to expose regions of interest for examination and/or measurement and produce an accurate image that reflects the fabrication process without damaging the regions of interest or creating artifacts in the exposed surface.

SUMMARY OF THE INVENTION

An object of the invention is to expose buried features for examination while minimizing the damage to those features.

Embodiments of the invention remove material to leave a hole adjacent to a feature of interest and fill the hole with deposited material to create a "bulkhead." An ion beam directed in part through the deposited material exposes a portion of the feature of interest. By directing the beam through the deposited material, artifacts are reduced and the exposed surface more accurately represents the structure as it looked before exposure. In some embodiments, the portion of the feature of interest is exposed by milling at a glancing angle to the surface.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIGS. 2A-2E illustrate the actions of the flowchart of FIG. 1;

DETAILED DESCRIPTION OF PREFERRED EMBODIMENTS

Figure 1:
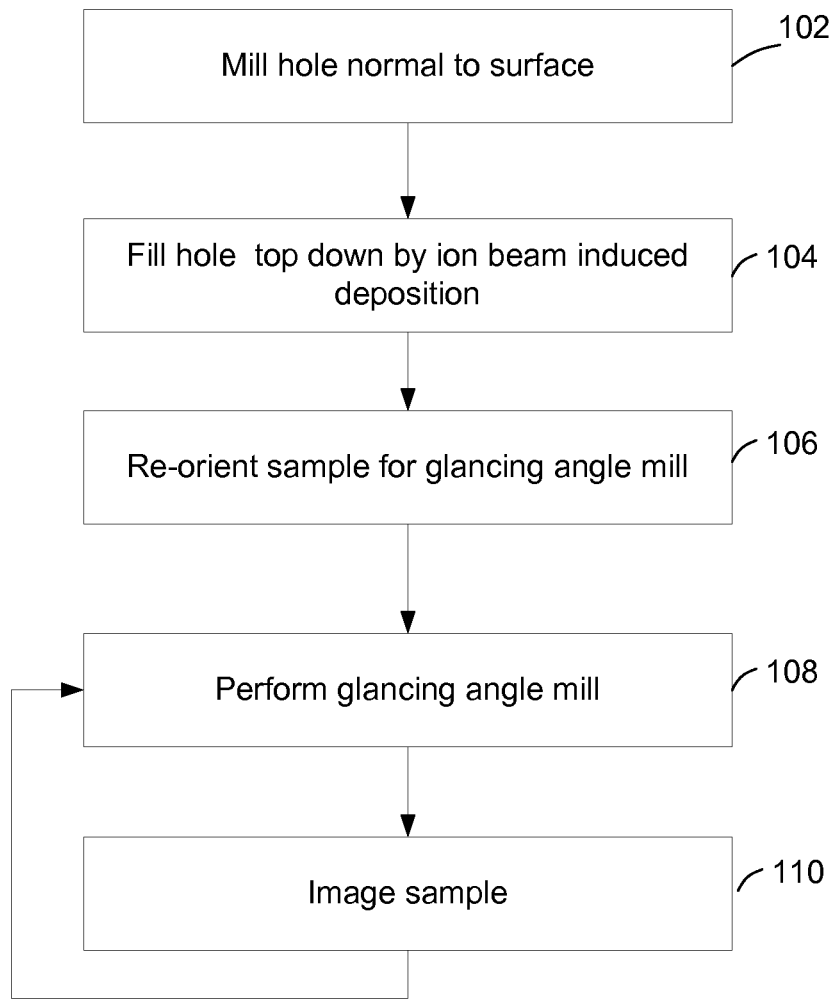
FIG. 1 is a flowchart showing a method of the present invention.

Embodiments of the invention use an ion beam to mill out a portion of a sample adjacent a region or feature of interest to create a trench into which a "bulkhead" is deposited. A "bulkhead" is a material through which the ion beam travels before milling a region of interest. The bulkhead is typically a solid block of material. The deposition adjacent, rather than on top of, the region of interest protects the edge of the region of interest in the beam direction during milling. Some embodiments provide the combination of tilt angle milling in conjunction with an adjacent protective deposition. Whereas the prior art teaches depositing a protective layer above the feature on an existing surface, embodiments of the invention mill produce a new surface onto which the material is deposited adjacent instead of above, the feature of interest. The terms "region of interest," "structure of interest," and "feature of interest" are used interchangeably herein.

Some embodiments of the invention provide particular advantages on a sample that has high aspect ratio holes or trenches that are unfilled. Some embodiments mill a hole with the FIB adjacent to the deep hole or holes that are to be characterized. The milled hole is filled with a deposited material. The deposited material acts as a mask to prevent the formation of curtaining when milling in a tilted orientation, either glancing angle or tilted cross section, through the bulk head. The deposited material is substantially uniform throughout the bulkhead, and so reduces curtaining.

Embodiments of the bulkhead are typically thick deposits that are positioned next to the region of interest in a horizontal plane, not on top of the region of interest, and the material is typically deposited into holes or trenches milled for this purpose. The milling to expose the region of interest is then not top down, but has a horizontal component through the bulkhead. While ion beam-induced deposition is used in the example below, any suitable method of deposition can be used. For example, other different types of induced deposition, in which a beam, such as a laser beam or an electron beam, decomposes a precursor to deposit a material, can be used, as well as direct deposition, such as cluster beam deposition, in which the material is deposited without decomposing a precursor.

The preferred dimensions of a bulkhead depend on the depth and angle of the mill, which is determined by the feature of interest that is being exposed. The width of the bulkhead should be at least as wide as the region of interest. The beam preferably passes through uniform material prior to milling all or a substantial portion of the feature of interest. If the bulkhead is gets too thin at some point in the milling, curtaining could occur. The shape of the bulkhead is preferably the minimum volume that presents a uniform material to the beam before it enters the region of interest. That is, the bulkhead should be sufficiently long and deep so that when the angled beam contacts the bottom of the region of interest, the beam is still travelling through a substantial length of bulkhead.

Figure 16:
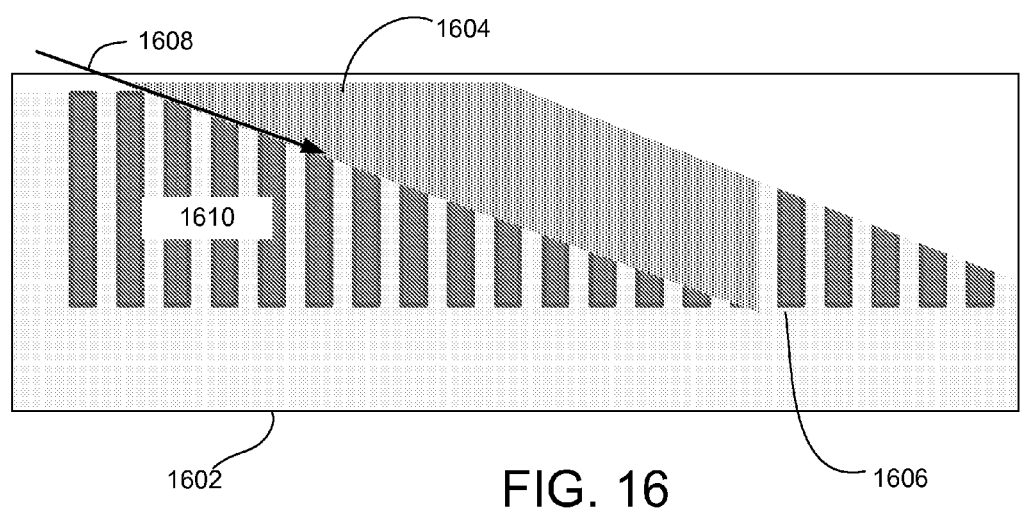
FIG. 16 shows a bulk head for efficiently producing artifact-free cross sections.
Figure 17:
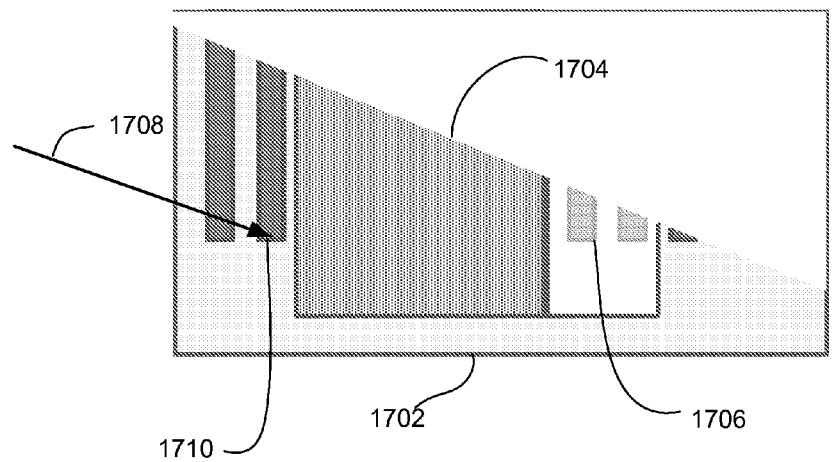
FIG. 17 shows a non-optimum bulk head.

The bulkhead does not have to be a rectangular box. A sloped pattern would be most efficient but more complex to create. For example, FIG. 16 shows an efficient bulkhead design that reduces curtaining without excessive deposition. Sample 1602 includes a deposited bulkhead 1604 and a feature of interest 1606. As shown by the arrow 1608, when the beam is milling the bottom of the feature of interest, the beam is passing through the bulkhead. Any extension of the bulkhead through an area, such as region 1610, through which the beam will not pass, does not improve milling and unnecessarily increases processing time. FIG. 17 shows a sample 1702 having a non-optimum bulkhead 1704 and a feature of interest 1706. The beam 1708 will encounter a non-uniform density in its path at the bottom of feature 1710, which will cause non-uniform milling of the bulkhead which, in turn, could cause non-uniform milling of a feature of interest on the other side of the bulkhead.

Existing methodologies involving CD-SEM, scatterometry, and TEM fail to characterize open hole dimensions on complex material stacks due to reasons involving depth, too complex/too many variables, and sample integrity, respectively. Embodiments of the invention described provide the ability to characterize open hole dimensions on complex material stacks.

Three embodiments used for bulkhead deposition for empty structure sample preparation are described below:
1. Slice and view-type, glancing type mill process;
2. An angled deposition process for a glancing type mill; and
3. An angled mill process that exposes a vertical plane for observation, rather than a glancing angle plane.

Method 1—Slice and View with Glancing Angle Mill

Figure 15:
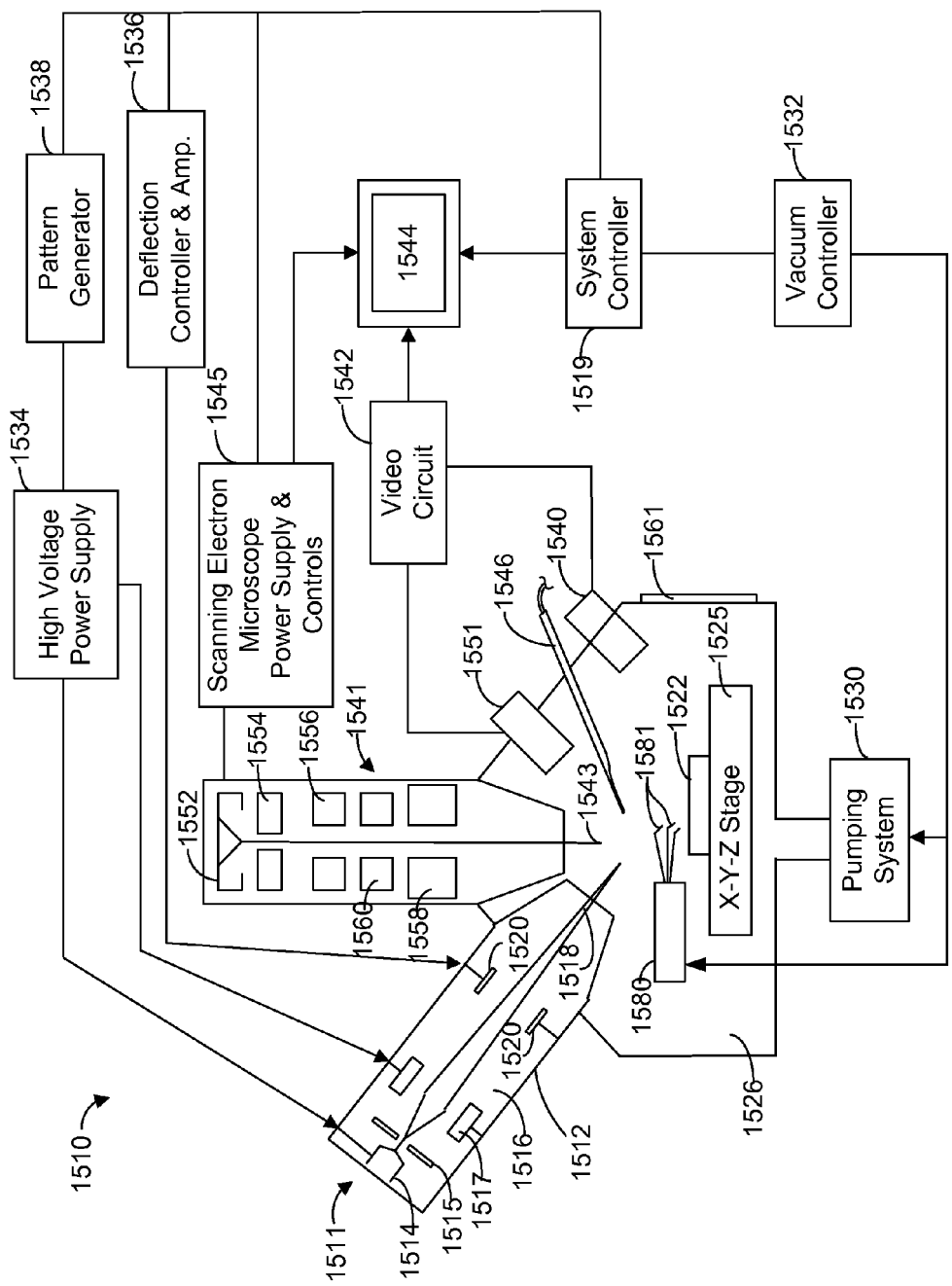
FIG. 15 shows a typical dual beam system on which embodiments of the invention can be practiced.

In the processes described below, an electron column of an SEM is mounted vertically and a FIB is mounted at 52 degrees. Such as system is shown in FIG. 15 and described in detail below. The angles described below are with respect to that configuration. When using other configurations, different angles will be used, but in some embodiments, the same relative angles will be used.

Figure 3A:
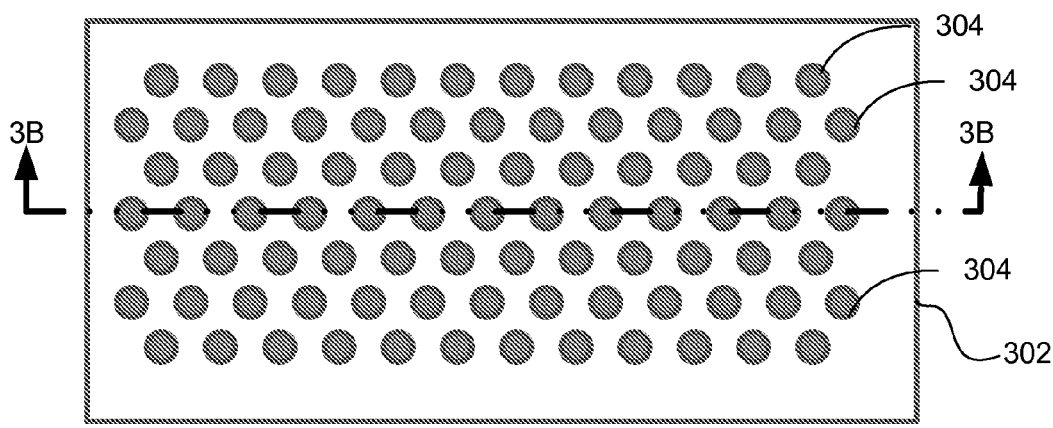
FIG. 3A shows a top down view of a sample before processing.
Figure 3B:
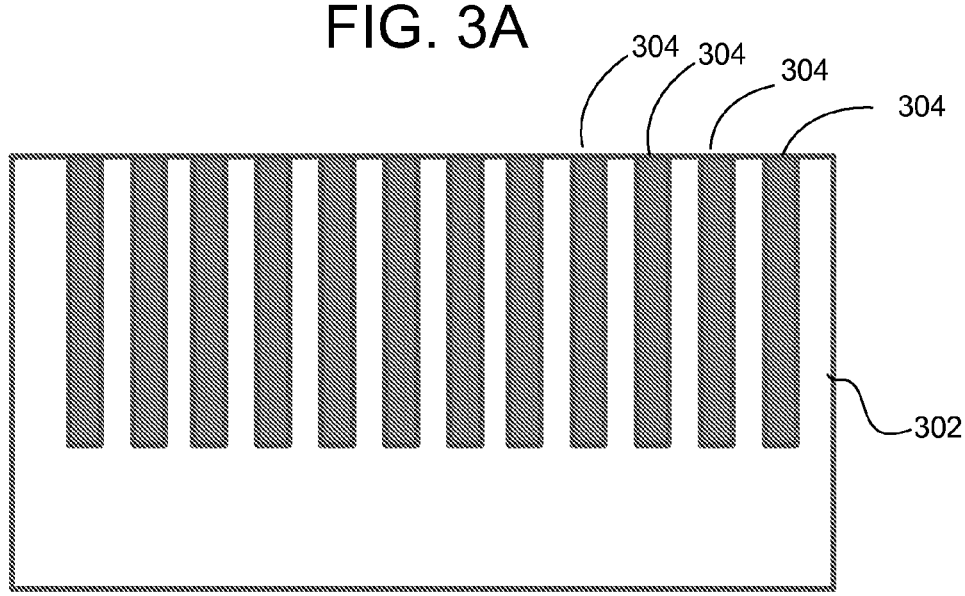
FIG. 3B shows a cross-sectional view of the sample of FIG. 3A.
Figure 4A:
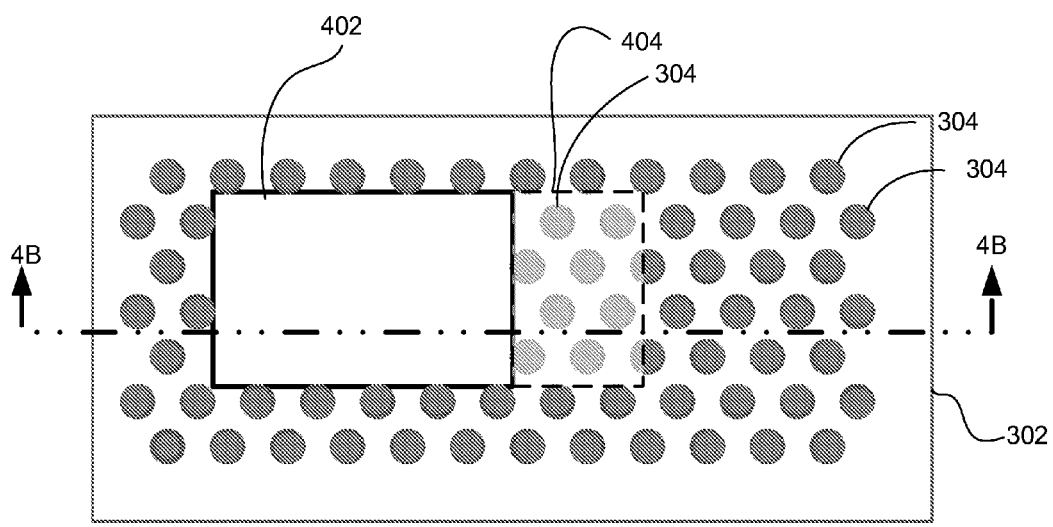
FIG. 4A shows a top down view of a sample having a hole milled.
Figure 4B:
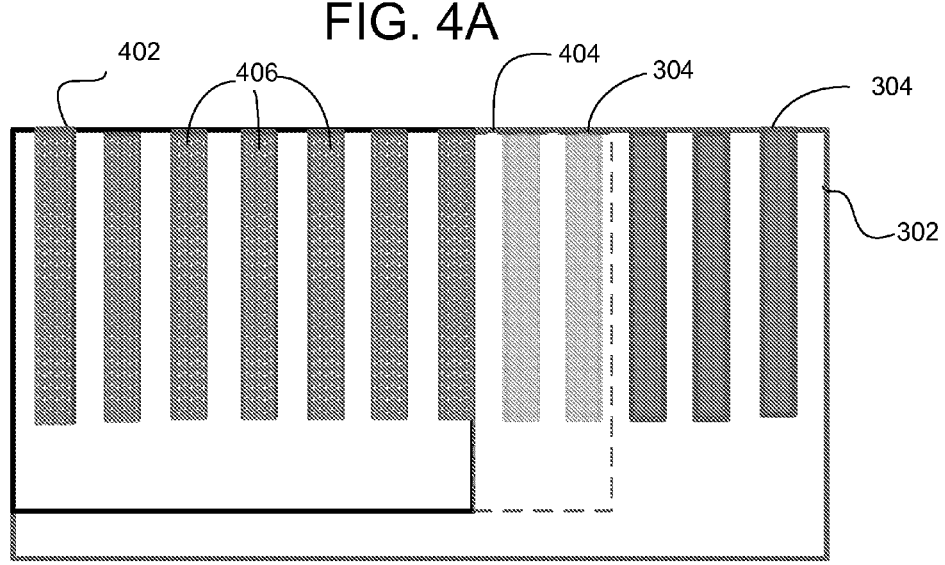
FIG. 4B shows a cross-sectional view of the sample of FIG. 4A.
Figure 5A:
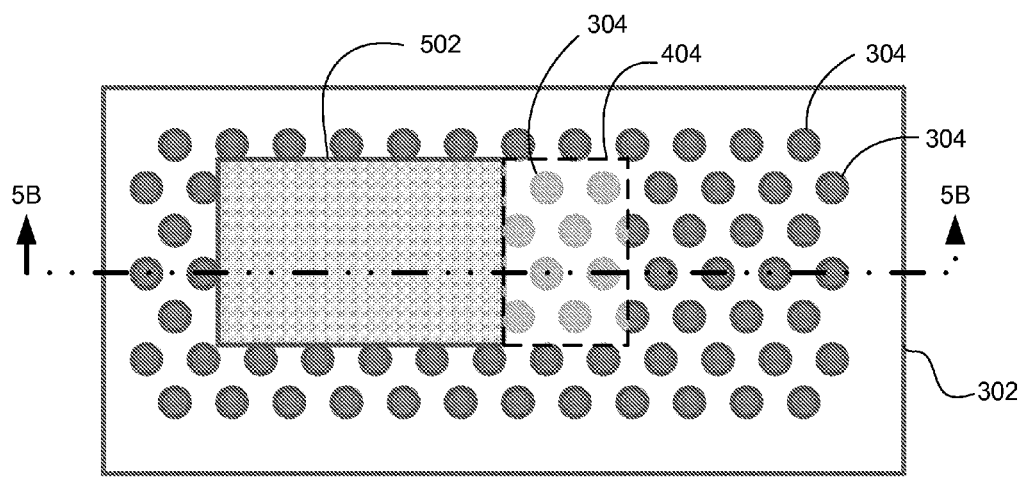
FIG. 5A shows a top down view of a sample having the hole filled with deposited material.
Figure 5B:
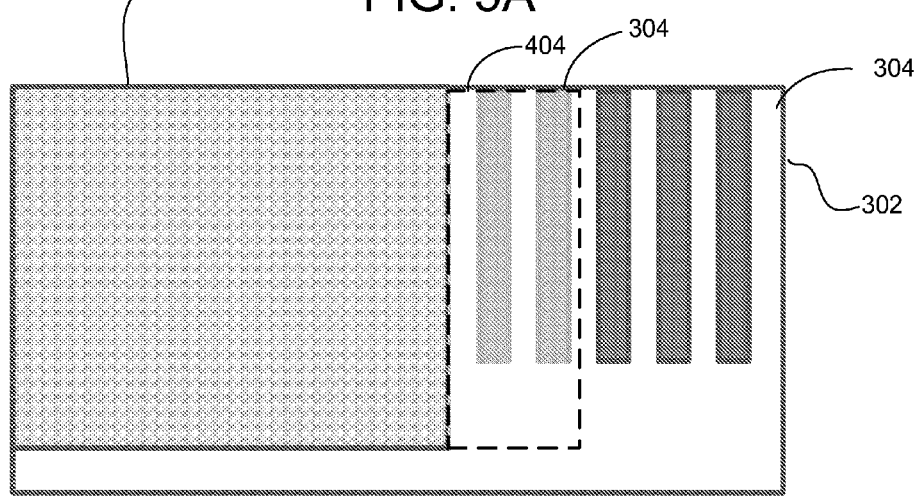
FIG. 5B shows a cross-sectional view of the sample of FIG. 5A.

FIG. 1 is a flowchart showing an embodiment of the invention. FIGS. 2A-2E show the ion beam and electron beam at each of the steps. FIG. 3A shows a top down view of a sample 302 that will undergo the process and FIG. 3B shows a cross-sectional side view taken through line 3B-3B of FIG. 3A. This convention of identifying cross section is used throughout this description. Sample 302 includes multiple high aspect ratio structures, such as open holes 304, trenches, or other high aspect ratio unfilled structures. In step 102, a hole is milled adjacent to the structure of interest from the top downward, that is, normal to the work piece surface, using a FIB as shown in FIG. 2A. FIGS. 4A and 4B show the hole 402 next to a structure of interest 404. Open holes 406 can be seen in the background of the region where the hole is milled in FIG. 4B. In step 104, the hole is filled from the top down of the sample using, for example, ion beam-induced deposition as shown in FIG. 2B. FIGS. 5A and 5B show the deposited material 502. Some of the deposition material will likely deposit over the area of interest. The hole can be filled for example, with tungsten, platinum, an oxide or other material that can be deposited using ion beam-induced deposition. The deposited material preferably has the same etch rate, for example, within 30%, or a lower etch rate, than the work piece material. Deposition precursors are well known.

In step 106, the sample is reoriented for glancing angle mill and is milled. Glancing angle milling is described in detail in U.S. patent application Ser. No. 13/609,811, filed Sep. 11, 2012 for "Glancing Angle Mill," which is hereby incorporated by reference. In step 108, a glancing angle mill is performed as shown in FIGS. 2C-2E. Preferably the glancing angle is 10° or less, more preferably 5° or less, even more preferably 3° or less, and in some cases, less than 1°. As used herein, a glancing angle mill will refer to milling a sample with the angle between the ion beam and the top surface of the being 10° or less. The invention is not limited to glancing angle milling. Beam angles of up to 45° or even greater angles are useful for some applications.

The actual angle used will depend on the configurations available on the system being used and the depth of the measurement to be made. For example, a typical copper interconnect trench is 12 nm deep. The tilt of sample stage is adjusted so that the angle between ion beam and sample will make a cut that is 12 nm deep at the far end of target area. That is, the angle and depth may be set to completely expose a feature. Although in the embodiment of FIGS. 2C-2E, the ion beam is directed at the very upper surface of the sample, in some preferred embodiments the beam could be directed deeper into the sample to expose more deeply buried features in much the same fashion.

Figure 6A:
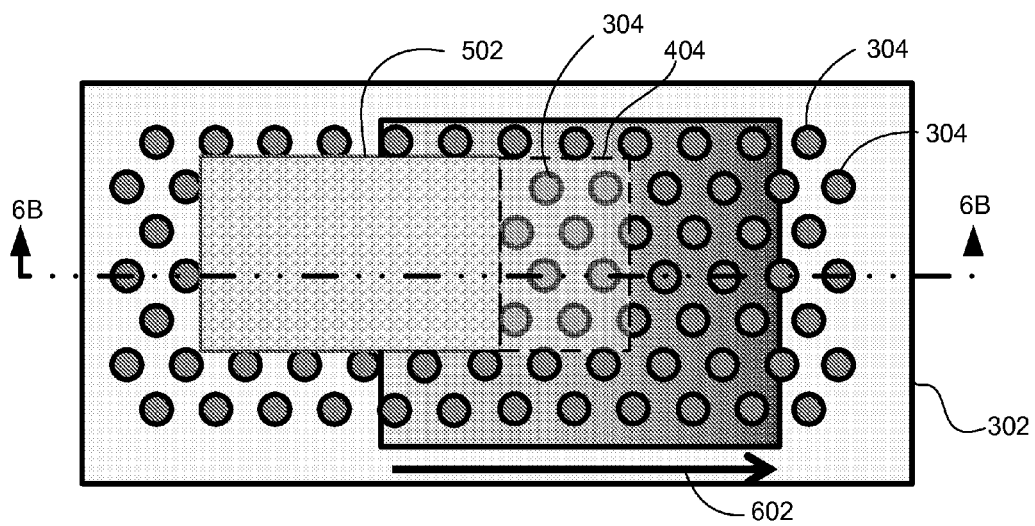
FIG. 6A shows a top down view of a glancing angle mill performed on the sample.
Figure 6B:
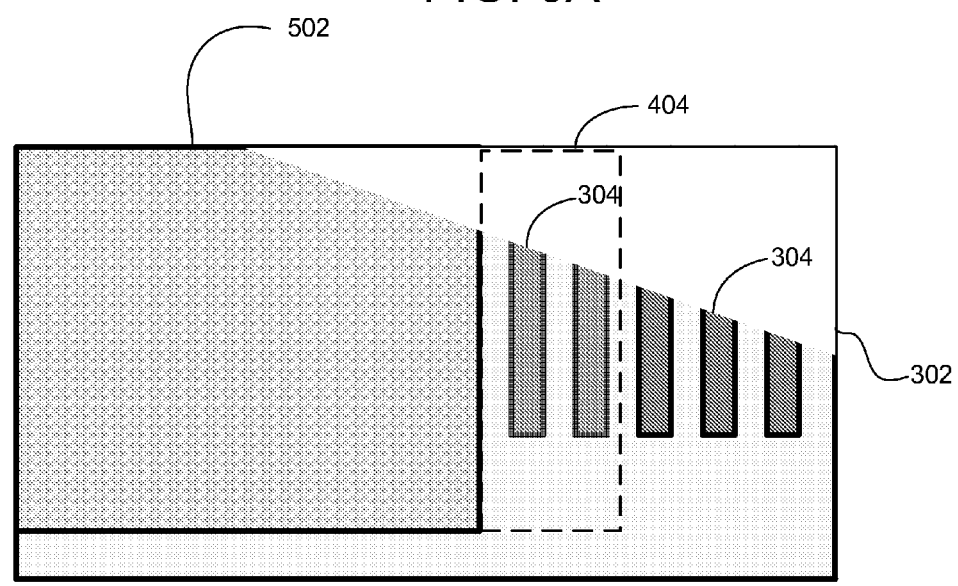
FIG. 6B shows a cross-sectional view of the sample of FIG. 6A.

FIGS. 6A and 6B show the result of the glancing angle mill. The horizontal component of the beam direction is shown by arrow 602, with the vertical component of the beam direction being into the page. Mill depth is increased from left to right across the bulkhead deposition into the area of interest, as shown by the shading that gets progressively darker from left to right in the milled region of FIG. 6A. After the glancing angle mill, in step 108, the cross section face is viewed using the SEM in step 110 to image the sample from the top down. The SEM is oriented nearly orthogonally to the structures to maintain high quality image by reducing the working distance. Milled regions located relatively far away from the deposition are subject to curtaining effects, while sample regions closer to the deposited region show little or no curtaining or other deformation. It is desirable, therefore, that the bulkhead be very close to the feature of interest.

Figure 7A:
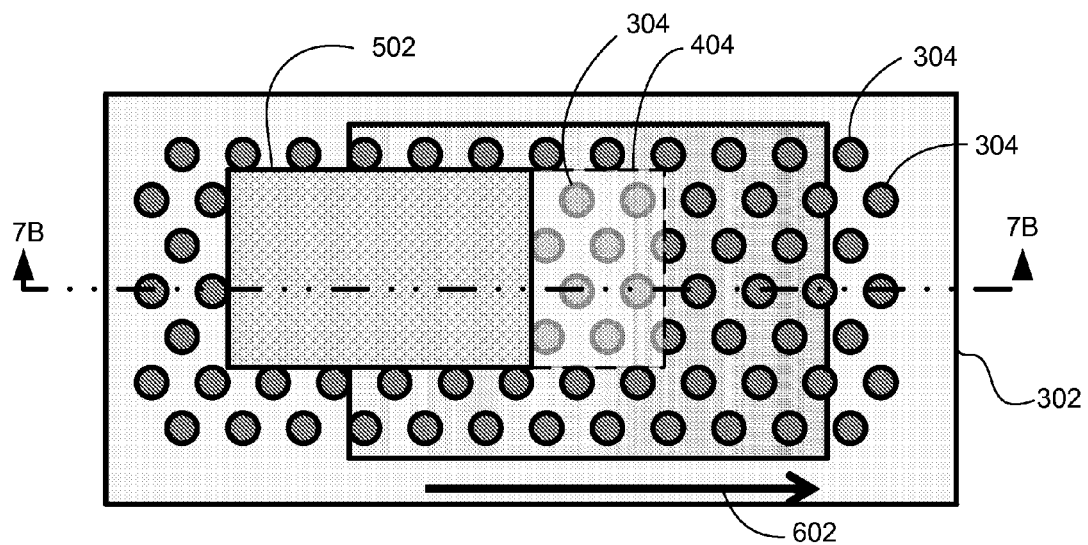
FIG. 7A shows a top down view of the sample of FIG. 6A with an additional glancing angle mill.
Figure 7B:
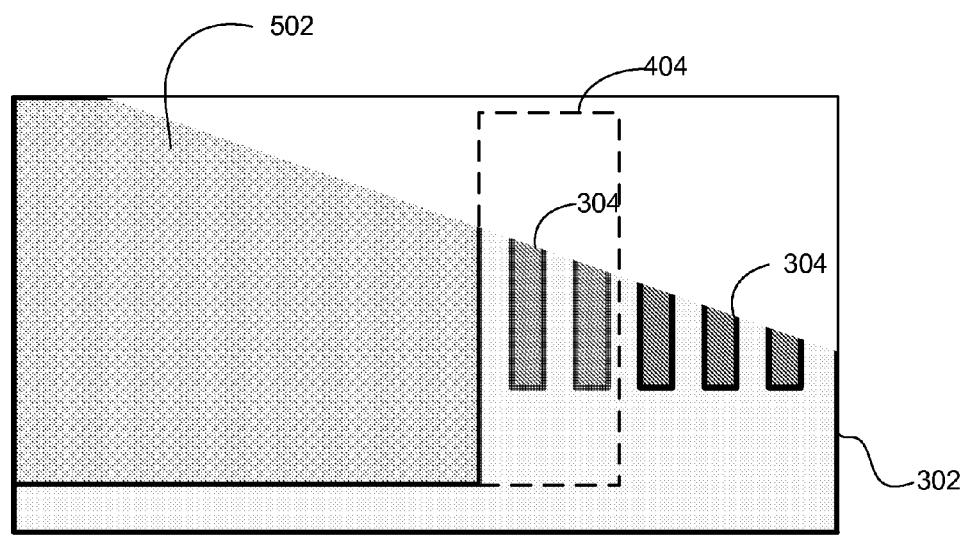
FIG. 7B shows a cross-sectional view of the sample of FIG. 7A.
Figure 8A:
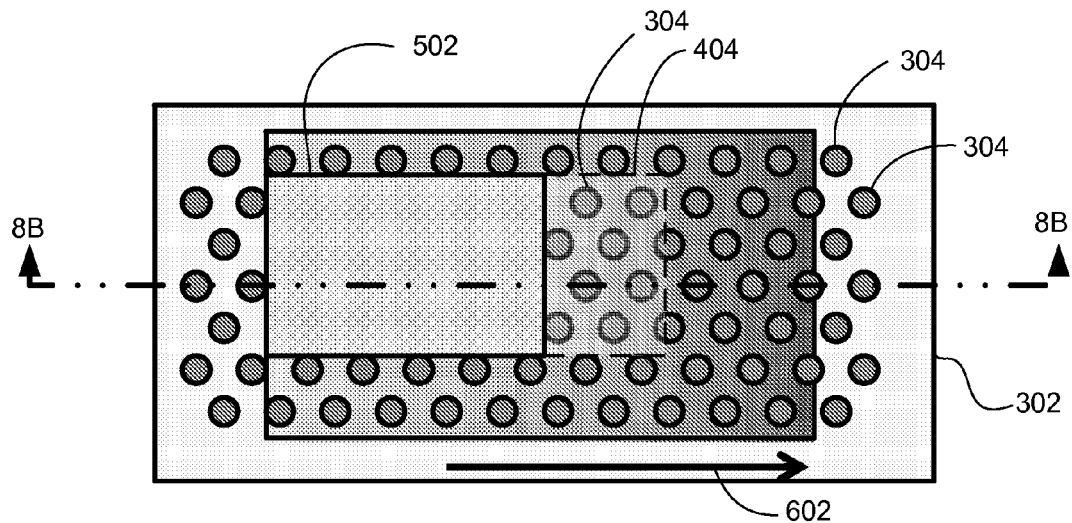
FIG. 8A shows a top down view of the sample of FIG. 7A with an additional glancing angle mill.
Figure 8B:
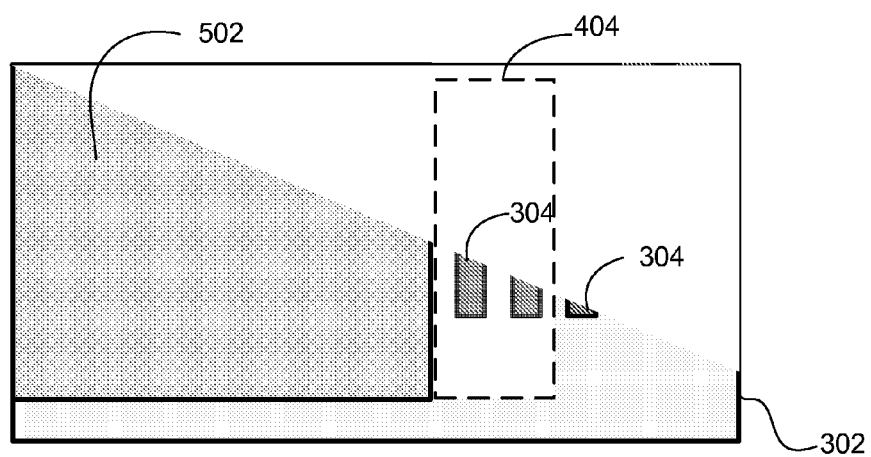
FIG. 8B shows a cross-sectional view of the sample of FIG. 8A.

Steps 108 and 110 are repeated to perform "slice and view," thereby providing images at various depths of the feature and the images can be combined to obtain three-dimensional information. FIG. 2D show a subsequent glancing angle mill that removes more material from the structures to produce the result shown in FIGS. 7A and 7B. FIG. 2E show a subsequent glancing angle mill that removes more material from the structures to produce the result shown in FIGS. 8A and 8B.

The repeated "slice and view" process will provide information at different depths. Each subsequent slice exposes a slightly deeper portion of the feature of interest close to the bulkhead. Since the glancing angle mill produces a deeper mill in the direction of the beam and, if there is a series of features of interest as shown in FIGS. 5B to 8B, the mill exposes different features of interest in the beam path at different depths. The further the feature is from the bulkhead, however, the more artifacts tend to be created. The best images are formed of the features closes to the bulkhead. Using multiple "slice and view" steps provides for the images of single structures at different depths. Slice and view provides better control of milling quality through better roundness of structures, greater control in diameter milling size, and creates a greater correlation to depth when milling. The repetitive slice and view images can be combined to form a three-dimensional image of a feature.

Method 2—Angled Bulkhead Deposition

In some samples, the region of interest has multiple rows of identical features. As shown above, in FIG. 6B for example, the glancing angle mill exposes different ones of the identical features at different depths below the surface. The features in the rows that are not adjacent to the bulkhead, especially if there are intervening features between the bulkhead and the feature of interest, will suffer from curtaining. Only features in the row nearest the bulkhead produce the best images, and those features are all cut to the same depth in the previous embodiment.

The edge of the bulkhead closest to region of interest is referred to as the "proximal edge." In some embodiments, the ion beam milling is such that the proximal edge is milled so that different points on the proximal edge have different depths below the original surface during the mill process. In some embodiments, some parts of the proximal edge are further from the beam source than other parts, and so the beam, which is angled into the work piece, causes the points of the edge that are further from the beam source to be milled deeper that parts that are closer. That is, the bulkhead has a proximal edge that is not parallel to a line of equal mill depth on the sloped surface produced by the ion beam milling. In some applications, this means that the proximal edge is not parallel to the glancing angle mill beam scan direction. A bulkhead that is milled so that different points on the proximal edge have different depths below the original surface during the mill process is referred to as an "angled bulkhead" because the proximal edge is not perpendicular to the beam direction.

If the points of the proximal edge of the bulkhead are milled to different depths, then each of the features of interest adjacent the proximal edge bulkhead is also milled to a different depth, thereby providing artifact-free viewing of different depths from a single milling operation.

In this embodiment, a FIB mills from above a hole to create a hole which is filled in to create an angled bulkhead. This embodiment allows properties, such as roundness and diameter of the feature to be correlated to depth with a single glancing angle mill. This embodiment can also be used with slice and view, to provide images at different depths of the same feature.

Figure 9:
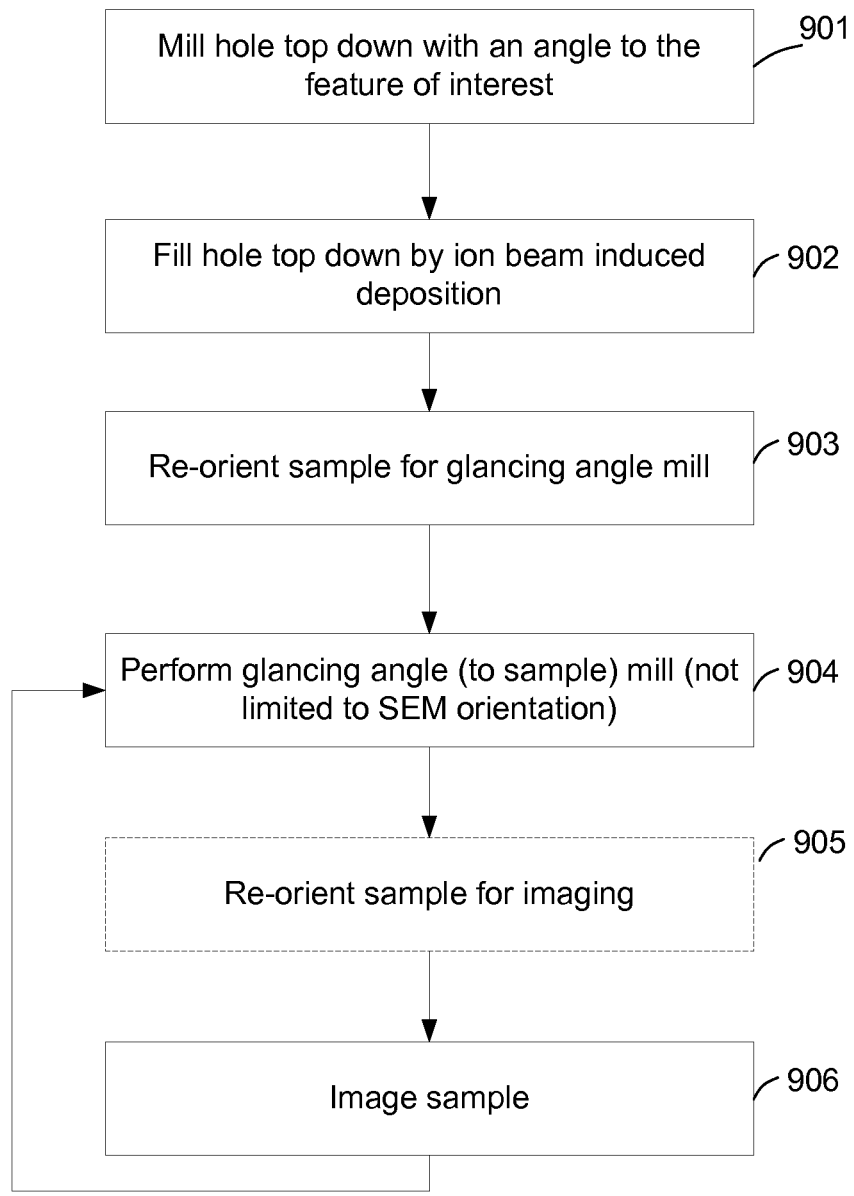
FIG. 9 is a flowchart of a second embodiment of the invention using angled deposition.

FIG. 9 is a flow chart showing the steps of this method, and FIGS. 10A, 10B, 11A, 11B, 12A, and 12B show a work piece 1002 that contain post-etch, unfilled structures 1004 as the region of interest 1008 to be observed. In step 901, a hole is milled top down at an angle to the scan direction of the ion beam. In step 902, the hole is filled top down by ion beam-induced deposition of a material to create an angled bulkhead 1006. In step 903, the sample is reoriented for glancing angle milling.

Figure 10A:
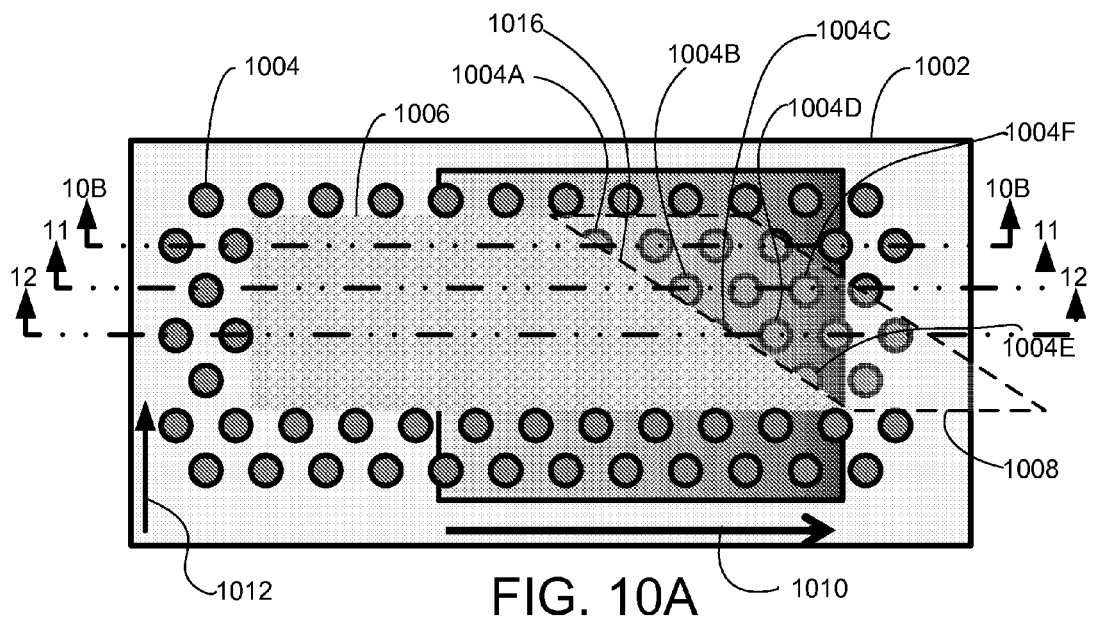
FIG. 10A shows top down views of progressive glancing angle mills.

In step 904, glancing angle milling is performed as described above with respect to the first embodiment. FIG. 10A shows a top view of the results of the glancing angle milling. Arrow 1010 shows the horizontal component of beam direction, which also has a component into the page. Arrow 1012 shows the scan direction of the beam. A vertical line on the drawing would correspond to a line of equal milling depth, which, as shown by the shading, gets deeper from left to right. The proximal edge 1016 of the bulkhead cuts across, that is, is angled with respect to, the line of equal milling depth. Unfilled structures 1004A, 1004B, 1004C, 1004D, and 1004E are all adjacent the bulkhead and their cross sections will have little or no curtaining artifact. Other unfilled structures, such as unfilled structure 1004F, will have curtaining because there are other two unfilled structures between the bulkhead and structure 1004F.

Figure 10B:
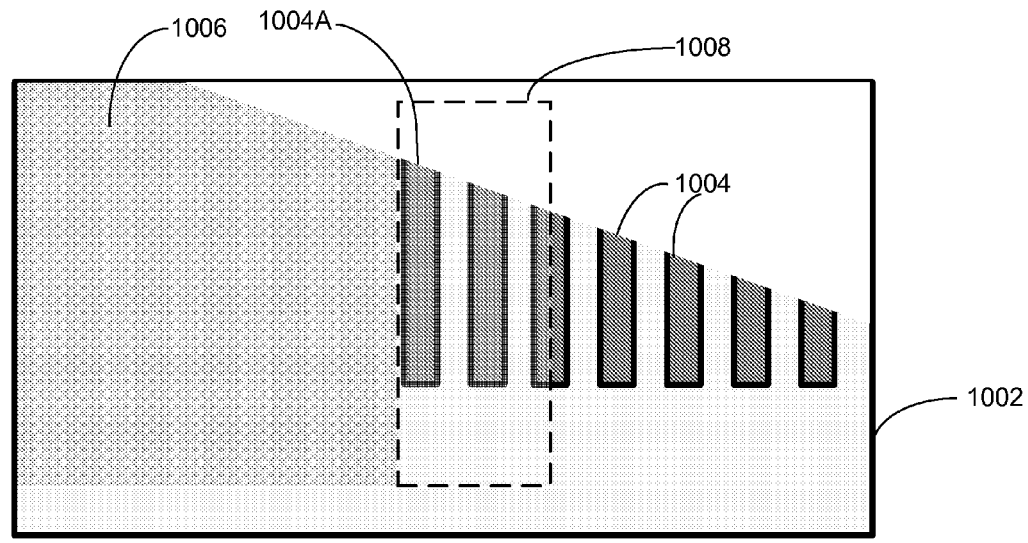
FIG. 10B shows a cross-sectional view of FIG. 10A.
Figure 11:
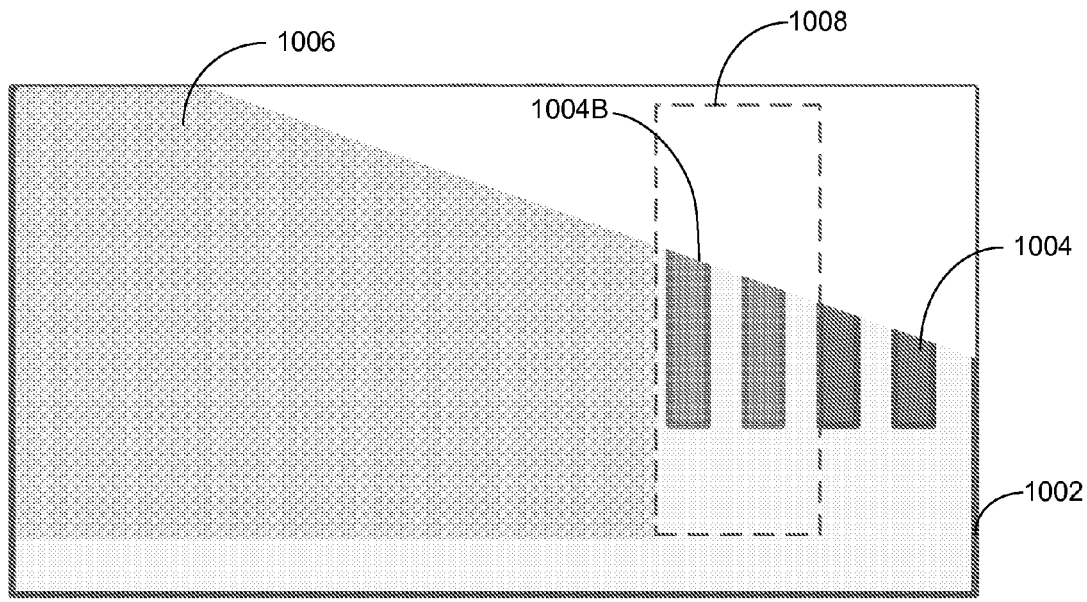
FIG. 11 shows another cross-sectional view of FIG. 10A.
Figure 12:
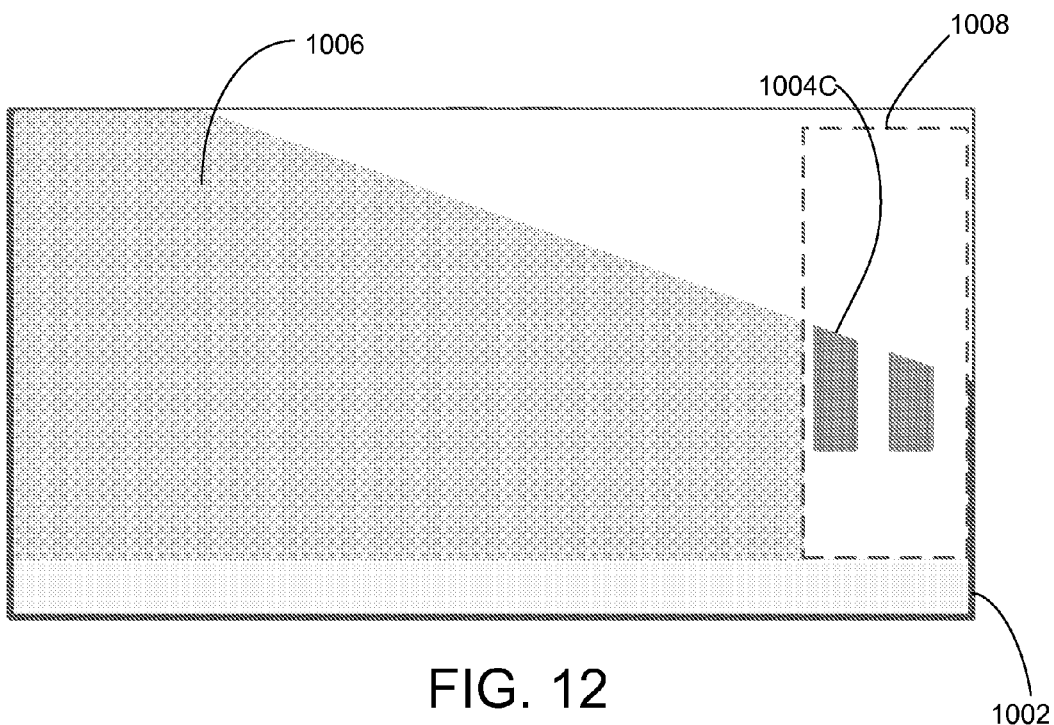
FIG. 12 shows another cross-sectional view of FIG. 10A.

FIGS. 10B, 11, and 12 show cross sections taken through different planes of FIG. 10A. The different cross sections show that a single glancing angle milling step exposes each of the unfilled structures 1004A, 1004B, 1004C, 1004D, and 1004E at a different depth below the surface. Unlike the previous embodiment, in which FIGS. 6-8 represent the sample after multiple sequential milling steps, FIGS. 10A, 10B, 11, and 12 represent different cross sections of the sample after a single milling step using an angled bulkhead.

In optional step 905, the sample is reoriented for imaging in step 906 by the electron beam. The sample orientation for glancing angle milling is not limited by the orientation of SEM. Different desired glancing mill angles allows for different orientation with respect to the SEM. One embodiment of the present invention would allow for the SEM to have a top down view. Vertical orientation of the SEM allows the SEM lens to be close to the structures to reduce working distance and provide higher quality imaging.

Benefits to utilizing this method allows for accurate analysis at different depths with a single cut and allows the correlation of characteristics such as roundness and diameter to depth. The embodiment can also be used with repetitive slice and view to provide information at different depths for the same feature.

Method 3—Bulkhead deposition protection for angled mill

Figure 13:
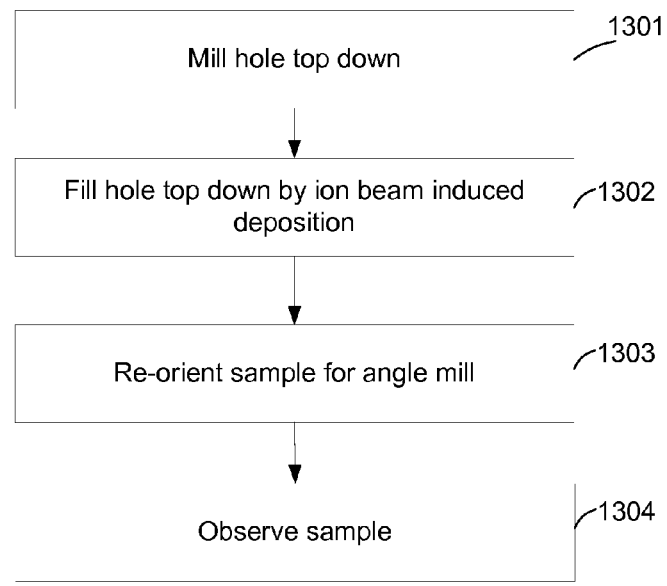
FIG. 13 is a flow chart showing the steps of a third embodiment of the invention using bulkhead deposition protection plus angled milling.
Figure 14A:
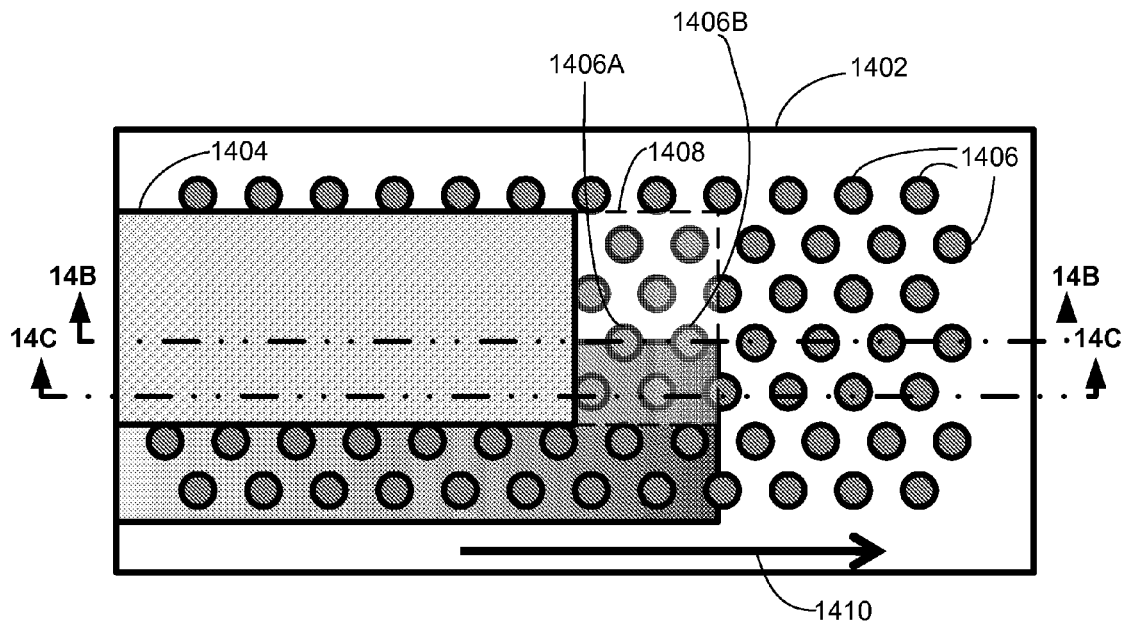
FIG. 14A shows a top down view of bulkhead deposition protection for angled mill.
Figure 14B:
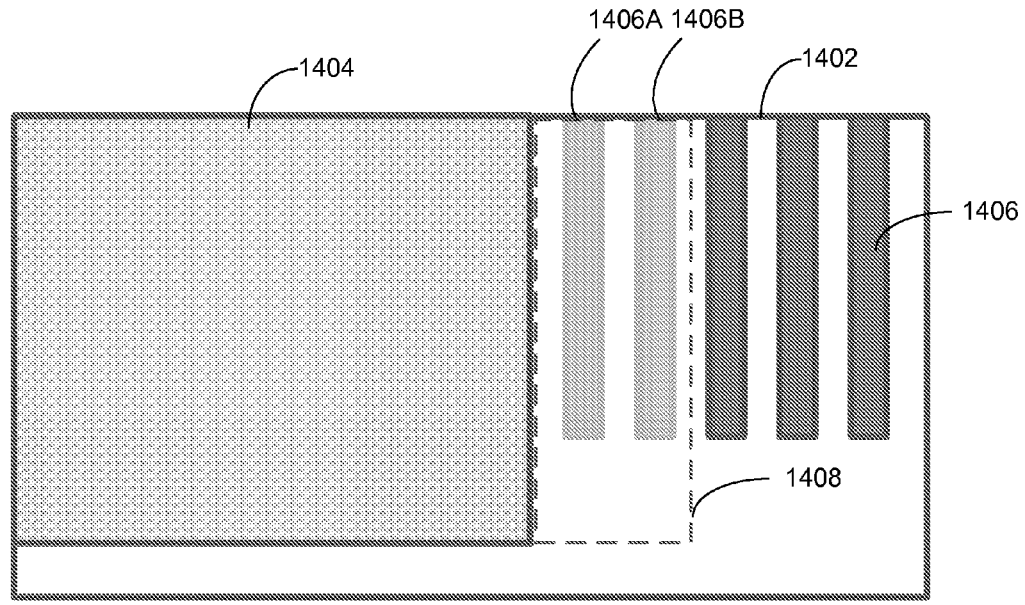
FIG. 14B shows a cross-sectional view of bulkhead deposition protection for angled mill.
Figure 14C:
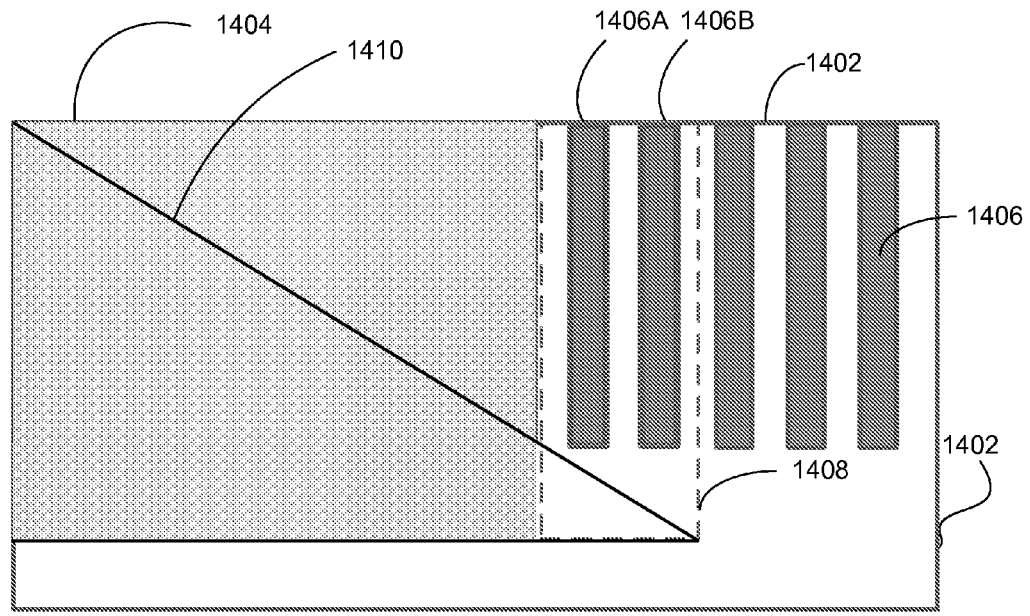
FIG. 14C shows another cross-sectional view of bulkhead deposition protection for angled mill.

FIG. 13 shows the steps of another embodiment of the invention. FIG. 14A shows a top view of a work 1402 piece being processed in accordance with the steps of FIG. 13, and FIGS. 14B and 14C show cross sections of the work piece 1402, which includes multiple high aspect ratio structures, such as open holes 1406, trenches, or other high aspect ratio unfilled structures. In step 1301, a hole is milled in the sample using an ion beam, typically oriented normal to the surface. In step 1302, the hole, located adjacent to a region of interest 1408, is filled with a deposited material to produce a bulkhead 1404 as described with respect to the previous embodiments.

In the previous embodiments, the milling, oriented at a glancing angle to the surface, progressed into the work piece uniformly over the milling area from the top down. That is, the beam scanned back and forth across the milling area, with the scan line moving down deeper into the work piece in subsequent scans to produce an angled trench that gets progressively deeper.

In this embodiment, a sloped line is milled on the side of the region of interest to a desired milling depth, and then beam is scanned so that the milled face proceeds sideways toward the region of interest. As in the previous embodiments, a bulkhead deposited in the beam path before the region of interest prevents curtaining in the region of interest. The process results in a exposing a vertical face that shows a side view of the feature of interest, instead of the glancing angle top down view of the previous embodiments. That is, if the feature of interest is an unfilled tube, the previous embodiments expose a circular slice through the tube at one depth for observation from the top down, whereas this embodiment exposes a longitudinal slice through the tube that shows hole over its entire length for observation from the side. Because this embodiment is not producing a top-down view, the angle of the beam with respect to the work piece surface can be larger. In step 1303, the ion beam mills out a cross section through tilt mill orientation. In step 1304, the sample is reoriented and viewed with the SEM.

FIG. 14A shows a top down view of bulkhead 1404. Arrow 1410 shows the direction of the horizontal component of the ion beam, which is also angled into the page. The mill is shallower to the left, and deeper to the right, as shown by the shading. FIG. 14B shows a cross section of FIG. 14A at line 14B-14B where the milling is complete and the exposed feature 1406A and 1406B are ready to view from a position normal to the page. FIG. 14C shows a cross section taken at a plane that is already milled and that is in front of the plane to be viewed.

The line 1410 of FIG. 14C shows the plane at the bottom of the milled trench, so there is no material directly above lines 1410. The portion of the bulkhead 1404 below the mill line remains after milling. In the background of FIG. 14C can be seen the unmilled bulkhead 1404 and the unmilled portion of the sample that is exposed for viewing including the cross-sectioned features 1046A and 1406B.

The milling preferably begins sufficiently far from the region of interest to produce a large enough trench in front of the final cross section so that an electron beam can scan the cross section and secondary electrons can escape the trench be collected to form an image. Steps 1303 and 1304 can be repeated to perform "slice and view" to obtain multiple images as the region of interest is milled through from the side.

Dual Beam System

FIG. 15 shows a typical dual beam system 1510 suitable for practicing the present invention, with a vertically mounted SEM column and a FIB column mounted at an angle of approximately 52° from the vertical. Suitable dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 1541, along with power supply and control unit 1545, is provided with the dual beam system 1510. An electron beam 1543 is emitted from a cathode 1552 by applying voltage between cathode 1552 and an anode 1554. Electron beam 1543 is focused to a fine spot by means of a condensing lens 1556 and an objective lens 1558. Electron beam 1543 is scanned two-dimensionally on the specimen by means of a deflection coil 1560. Operation of condensing lens 1556, objective lens 1558, and deflection coil 1560 is controlled by power supply and control unit 1545.

Electron beam 1543 can be focused onto substrate 1522, which is on movable stage 1525 within lower chamber 1526. When the electrons in the electron beam strike substrate 1522, secondary electrons are emitted. These secondary electrons are detected by a secondary electron detector 1540 as discussed below.

Dual beam system 1510 also includes focused ion beam (FIB) system 1511 which comprises an evacuated chamber having an upper portion 1512 within which are located an ion source 1514 and a focusing column 1516 including extractor electrodes and an electrostatic optical system. The axis of focusing column 1516 is tilted 52 degrees from the axis of the electron column. The upper portion 1512 includes an ion source 1514, an extraction electrode 1515, a focusing element 1517, deflection elements 1520, and a focused ion beam 1518. Ion beam 1518 passes from ion source 1514 through focusing column 1516 and between electrostatic deflectors 1520 toward substrate 1522, which comprises, for example, a semiconductor device positioned on movable stage 1525 within lower chamber 1526.

Stage 1525 can preferably move in a horizontal plane (X and Y axes) and vertically (Z axis). Stage 1525 can also tilt approximately 60° and rotate about the Z axis. A door 1561 is opened for inserting substrate 1522 onto X-Y stage 1525 and also for servicing an internal gas supply reservoir, if one is used. The door is interlocked so that it cannot be opened if the system is under vacuum.

An ion pump (not shown) is employed for evacuating upper portion 1512. The chamber 1526 is evacuated with turbomolecular and mechanical pumping system 1530 under the control of vacuum controller 1532. The vacuum system provides within chamber 1526 a vacuum of between approximately $1 \times 10^{-7}$ Torr and $5 \times 10^{-4}$ Torr. If an etch-assisting gas, an etch-retarding gas, or a deposition precursor gas is used, the chamber background pressure may rise, typically to about $1 \times 10^{-5}$ Torr.

The high voltage power supply provides an appropriate acceleration voltage to electrodes in ion beam focusing column focusing 1516 for energizing and focusing ion beam 1518. When it strikes substrate 1522, material is sputtered, that is physically ejected, from the sample. Alternatively, ion beam 1518 can decompose a precursor gas to deposit a material.

High voltage power supply 1534 is connected to liquid metal ion source 1514 as well as to appropriate electrodes in ion beam focusing column 1516 for forming an approximately 1 keV to 60 keV ion beam 1518 and directing the same toward a sample. Deflection controller and amplifier 1536, operated in accordance with a prescribed pattern provided by pattern generator 1538, is coupled to deflection plates 1520 whereby ion beam 1518 may be controlled manually or automatically to trace out a corresponding pattern on the upper surface of substrate 1522. In some systems the deflection plates are placed before the final lens, as is well known in the art. Beam blanking electrodes (not shown) within ion beam focusing column 1516 cause ion beam 1518 to impact onto blanking aperture (not shown) instead of substrate 1522 when a blanking controller (not shown) applies a blanking voltage to the blanking electrode.

The liquid metal ion source 1514 typically provides a metal ion beam of gallium. The source typically is capable of being focused into a sub one-tenth micrometer wide beam at substrate 1522 for either modifying the substrate 1522 by ion milling, enhanced etch, material deposition, or for the purpose of imaging the substrate 1522. Other ion sources, such as a plasma ion source, can also be used.

An optional probe assembly includes a probe motion mechanism 1580 and probe tips 1581 that allow applying or sensing a voltage at an exposed conductor. The probe tips can be moved individually to a desired position and lowered to contact the substrate 1522. While three probe tips are shown, the number of probe tips can vary. Multiple probe motion mechanism can be used to control any number of probes. The probe tips can apply a voltage or current to the substrate 1522 at a precise location and/or can sense a voltage or current.

A charged particle detector 1540, such as an Everhart-Thornley detector or multi-channel plate, used for detecting secondary ion or electron emission is connected to a video circuit 1542 that supplies drive signals to video monitor 1544 and receives deflection signals from controller 1519. The location of charged particle detector 1540 within lower chamber 1526 can vary in different embodiments. For example, a charged particle detector 1540 can be coaxial with the ion beam and include a hole for allowing the ion beam to pass. In other embodiments, secondary particles can be collected through a final lens and then diverted off axis for collection.

An optical microscope 1551 allows observation of the sample 1522 and the probes 1581. The optical microscope may be co-axial with one of the charged particle beams, as described, for example, in U.S. Pat. No. 6,373,070 to Rasmussen, for "Method apparatus for a coaxial optical microscope with focused ion beam," is owned by the application of the present application.

A gas delivery system 1546 extends into lower chamber 1526 for introducing and directing a gaseous vapor toward substrate 1522. U.S. Pat. No. 5,851,413, to Casella et al. for "Gas Delivery Systems for Particle Beam Processing," assigned to the assignee of the present invention, describes a suitable gas delivery system 1546. Another gas delivery system is described in U.S. Pat. No. 5,435,850, to Rasmussen for a "Gas Injection System," also assigned to the assignee of the present invention. For example, a metal organic compound can be delivered to the beam impact point to deposit a metal upon impact of the ion beam or the electron beam. A precursor gas, such as $(CH_3)_3Pt(C_pCH_3)$ to deposit platinum or tungsten hexcarbonyl to deposit tungsten, can be delivered to be decomposed by the electron beam to provide the protective layer in step 108.

A system controller 1519 controls the operations of the various parts of dual beam system 1510. Through system controller 1519, a user can cause ion beam 1518 or electron beam 1543 to be scanned in a desired manner through commands entered into a conventional user interface (not shown). Alternatively, system controller 1519 may control dual beam system 1510 in accordance with programmed instructions. A preferred controller is in communication with or includes a memory that stores instructions for automatically carrying out the steps of FIG. 1, 9, or 13. System controller 1519 can be used to control the probe motion assembly 1580. In some embodiments, dual beam system 1510 incorporates image recognition software, such as software commercially available from Cognex Corporation, Natick, Mass., to automatically identify regions of interest, and then the system can manually or automatically expose cross sections for imaging in accordance with the invention. For example, the system could automatically locate similar features on semiconductor wafers including multiple devices, and expose and form images of features of interest on different (or the same) devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Descriptions herein use the terms horizontal and vertical relative to a wafer or other work piece. It will be understood that "horizontal" typically us used to mean parallel to the work piece surface and the conductive planes deposited on to the work piece work piece, and "vertical" is typically used to mean orthogonal to the work piece surface.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

The present specification discloses both a method and an apparatus for performing the operations of the method. Such apparatus may be specially constructed for the required purposes, or may comprise a general purpose computer or other device selectively activated or reconfigured by a computer program stored in the computer. Various general purpose charged particle beam systems may be used with programs in accordance with the teachings herein. Alternatively, the construction of more specialized apparatus to perform the required method steps may be appropriate.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer or controller for a charged particle beam and effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ."

To the extent that any term is not specially defined in this specification, the intent is that the term is to be given its plain and ordinary meaning. The accompanying drawings are intended to aid in understanding the present invention and, unless otherwise indicated, are not drawn to scale.

The term "integrated circuit" refers to a set of electronic components and their interconnections (internal electrical circuit elements, collectively) that are patterned on the surface of a microchip. The term "semiconductor chip" refers generically to an integrated circuit (IC), which may be integral to a semiconductor wafer, separated from a wafer, or packaged for use on a circuit board. The term "FIB" or "focused ion beam" is used herein to refer to any collimated ion beam, including a beam focused by ion optics and shaped ion beams.

The embodiment above describes a 3D NAND-type structures, but the invention is not limited to such structures and is useful, for example, for DRAMS, and for characterizing trenches and other structures, as well as circular holes.

To the extent that any term is not specially defined in this specification, the intent is that the term is to be given its plain and ordinary meaning. The accompanying drawings are intended to aid in understanding the present invention and, unless otherwise indicated, are not drawn to scale.

Some embodiments of the invention provide a method of using a charged particle beam to expose a feature of interest, including:
  milling a trench adjacent to the feature of interest;
  filling the trench with a material using beam-induced deposition;
  directing an ion beam to expose the feature of interest from an angle that requires milling through the deposited material; and
  observing the exposed feature of interest.

In accordance with some embodiments, filling the trench with a material using beam-induced deposition comprises depositing material adjacent to but not on top of the feature of interest.

In accordance with some embodiments, directing an ion beam to expose the feature of interest from an angle that requires milling through the deposited material includes directing an ion beam to expose the feature of interest from an angle that is less than 10 degrees.

In accordance with some embodiments:
  the filled trench comprises a bulkhead;
  the bulkhead has a proximal edge closest to the feature of interest; and
  the bulkhead is configured such that directing an ion beam to expose the feature of interest causes each point to be milled to a different depth.

In accordance with some embodiments, the region of interest contains multiple identical features and in which directing an ion beam exposes multiple features of interest adjacent to the bulkhead at different depths in one exposed face.

In accordance with some embodiments, directing an ion beam to expose the feature of interest from an angle that requires milling through the deposited material comprises exposing a vertical face parallel to the beam direction to provide a side view of the feature of interest.

In accordance with some embodiments, directing an ion beam to expose the feature of interest from an angle that requires milling through the deposited material comprises exposing a face less than 10 degrees from the horizontal and parallel to the beam direction to provide a nearly top-down view of the feature of interest.

In accordance with some embodiments, the steps of directing an ion beam to expose the feature of interest from an angle that requires milling through the deposited material; and observing the exposed feature of interest are repeated to provide information about the feature at multiple depths below the original surface.

Some embodiments of the invention provide a method of exposing a feature of interest in a sample with a charged particle beam, the sample comprising a first material, the method comprising:

milling a hole adjacent to the feature of interest;
filling the hole with a second material; and
directing an ion beam from an angle that requires milling through the deposited material to expose the feature of interest.

In accordance with some embodiments, milling a hole adjacent to the feature of interest comprises milling the hole in a direction normal to the sample surface.

In accordance with some embodiments, filling the hole with a material comprises filling the hole using charged particle beam deposition.

In accordance with some embodiments, directing an ion beam to expose the feature of interest comprises performing a glancing angle mill.

In accordance with some embodiments, the method further comprises:
re-orienting the sample before performing a glancing angle mill; and
imaging the sample with an scanning electron microscope.

In accordance with some embodiments, the second material used to fill the hole has an etch rate within 30% of the etch rate of the first material.

In accordance with some embodiments, the feature of interest is a high aspect ratio structure.

In accordance with some embodiments, the second material used to fill the hole comprises tungsten, platinum, or an oxide.

In accordance with some embodiments, the method further comprises repeating, at least once, the steps of performing a glancing angle mill and imaging the sample with a scanning electron microscope.

In accordance with some embodiments, the information obtained from imaging the sample is combined to create three-dimensional information of the sample.

In accordance with some embodiments, milling a hole adjacent to the feature of interest comprises milling the hole having a proximal edge that is angled to the region of interest.

Some embodiments provide a system for exposing a feature of interest in a sample, comprising:
an ion optical column for providing a focused beam of ions;
an electron optical column for providing a focused beam of electrons;
a particle detector for detecting secondary particles emitted from the sample; and
a controller communicating to a computer memory, the computer memory storing instructions for:
milling a hole adjacent to the feature of interest;
filling the hole with a second material using charged particle beam deposition;
directing an ion beam to expose the feature of interest from an angle that requires milling through the deposited material, wherein milling through the deposited material comprises performing a glancing angle mill and re-orienting the sample before performing the glancing angle mill; and
imaging the sample using a scanning electron microscope.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of using a charged particle beam to expose a feature of interest in a sample, including:
milling a trench adjacent to the feature of interest in a surface of the sample;
filling the trench with a material using beam-induced deposition;
directing an ion beam to expose the feature of interest from an angle that requires milling through the deposited material, the angle being an angle between the surface and the ion beam that is less than or equal to 45°; and
observing the exposed feature of interest.

2. The method of claim 1 in which filling the trench with a material using beam-induced deposition comprises depositing material adjacent to but not on top of the feature of interest.

3. The method of claim 1 in which the angle is an angle between the surface and the ion beam that is less than or equal to 10°.

4. The method of claim 1 in which:
the filled trench comprises a bulkhead;
the bulkhead has a proximal edge closest to the feature of interest; and
the bulkhead is configured such that directing an ion beam to expose the feature of interest causes each point on the proximal edge to be milled to a different depth.

5. The method of claim 4 in which the region of interest contains multiple identical features and in which directing an ion beam exposes multiple features of interest adjacent to the bulkhead at different depths in one exposed face.

6. The method of claim 1 in which directing an ion beam to expose the feature of interest from an angle that requires milling through the deposited material comprises exposing a vertical face parallel to the beam direction to provide a side view of the feature of interest.

7. The method of claim 1 in which directing an ion beam to expose the feature of interest from an angle that requires milling through the deposited material comprises exposing a face less than 10 degrees from the horizontal and parallel to the beam direction to provide a nearly top-down view of the feature of interest.

8. The method of claim 7 in which the steps of directing an ion beam to expose the feature of interest from an angle that requires milling through the deposited material; and observing the exposed feature of interest are repeated to provide information about the feature of interest at multiple depths below the original surface.

9. A method of exposing a feature of interest in a sample with a charged particle beam, the sample comprising a first material, the method comprising:
milling a hole adjacent to the feature of interest in a surface of the sample;
filling the hole with a second material; and
directing an ion beam from an angle that requires milling through the second material to expose the feature of interest, wherein the angle is an angle between the surface and the ion beam that is less than or equal to 45°.

10. The method of claim 9 in which milling a hole adjacent to the feature of interest comprises milling the hole in a direction normal to the surface.

11. The method of claim 9 in which filling the hole with a material comprises filling the hole using charged particle beam deposition.

12. The method of claim 9 in which directing an ion beam to expose the feature of interest comprises performing a glancing angle mill.

13. The method of claim 12 further comprising:
re-orienting the sample before performing the glancing angle mill; and
imaging the sample with a scanning electron microscope.

14. The method of claim 9 in which the second material used to fill the hole has an etch rate within 30% of the etch rate of the first material.

15. The method of claim 9 in which the feature of interest is a high aspect ratio structure.

16. The method of claim 9 in which the second material used to fill the hole comprises tungsten, platinum, or an oxide.

17. The method of claim 13 further comprising repeating, at least once, the steps of performing a glancing angle mill and imaging the sample with a scanning electron microscope.

18. The method of claim 17 in which information obtained from imaging the sample is combined to create three-dimensional information of the sample.

19. The method of claim 9 in which milling a hole adjacent to the feature of interest comprises milling the hole to have a proximal edge that is angled with respect to the feature of interest.

20. A system for exposing a feature of interest in a sample, comprising:

an ion optical column for providing a focused beam of ions;

an electron optical column for providing a focused beam of electrons;

a particle detector for detecting secondary particles emitted from the sample; and a controller communicating to a computer memory, the computer memory storing instructions for:

milling a hole adjacent to the feature of interest in a surface of the sample;

filling the hole with a second material using charged particle beam deposition;

directing an ion beam to expose the feature of interest from an angle that requires milling through the deposited second material, the angle being an angle between the surface and the ion beam that is less than or equal to 10°, wherein milling through the deposited second material comprises performing a glancing angle mill and re-orienting the sample before performing the glancing angle mill; and imaging the sample using a scanning electron microscope.

* * * * *